(12) United States Patent
Dodge, Sr.

(10) Patent No.: US 6,449,825 B1
(45) Date of Patent: Sep. 17, 2002

(54) ROOF INSPECTION METHOD

(76) Inventor: Dennis M. Dodge, Sr., 5314 195th Ave. E., Bonney Lake, WA (US) 98390

( * ) Notice: Subject to any disclaimer, the term of this patent is extended or adjusted under 35 U.S.C. 154(b) by 0 days.

(21) Appl. No.: 09/441,790

(22) Filed: Nov. 17, 1999

(51) Int. Cl.[7] .............................. B23P 6/00; B23P 23/00; G01N 1/04
(52) U.S. Cl. ................. 29/402.01; 29/402.02; 29/407.01; 73/864.45
(58) Field of Search .................. 29/402.01, 402.02, 29/407.01; 73/864.45

(56) References Cited

U.S. PATENT DOCUMENTS

| | | | |
|---|---|---|---|
| 408,223 A | * | 8/1889 | Draper |
| 3,707,197 A | * | 12/1972 | Walesch et al. ............... 175/20 |
| 3,967,197 A | * | 6/1976 | Anderson ................. 324/61 R |
| 4,257,189 A | * | 3/1981 | Hensley ....................... 46/241 |

* cited by examiner

Primary Examiner—David P. Bryant
Assistant Examiner—John C. Hong
(74) Attorney, Agent, or Firm—Delbert J. Barnard

(57) ABSTRACT

A tool (20) is used to cut a sample (12', 52') from a roof covering (12, 52). The sample (12', 52') is inspected. A mastic is placed in the opening in the roof covering (12, 52) from which the sample (12', 52') came. The mastic forms a plug (50, 58) which closes and seals the sample opening (46, 56). The sample tool (20) has a lower end cutting edge (40). It also has handle parts (16, 18) which are connectable to the tool body (22). The handle parts are turned to cause a rotation of the tool body (22).

3 Claims, 4 Drawing Sheets

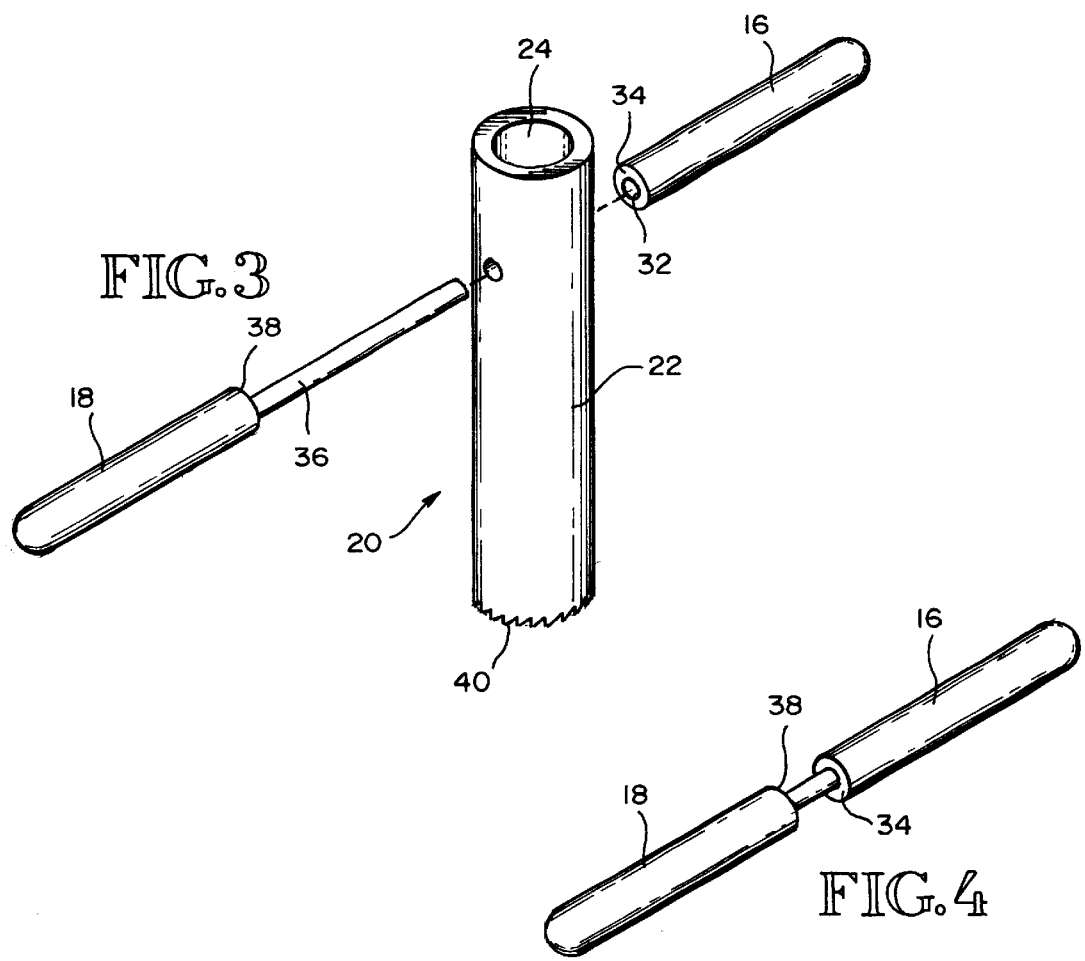
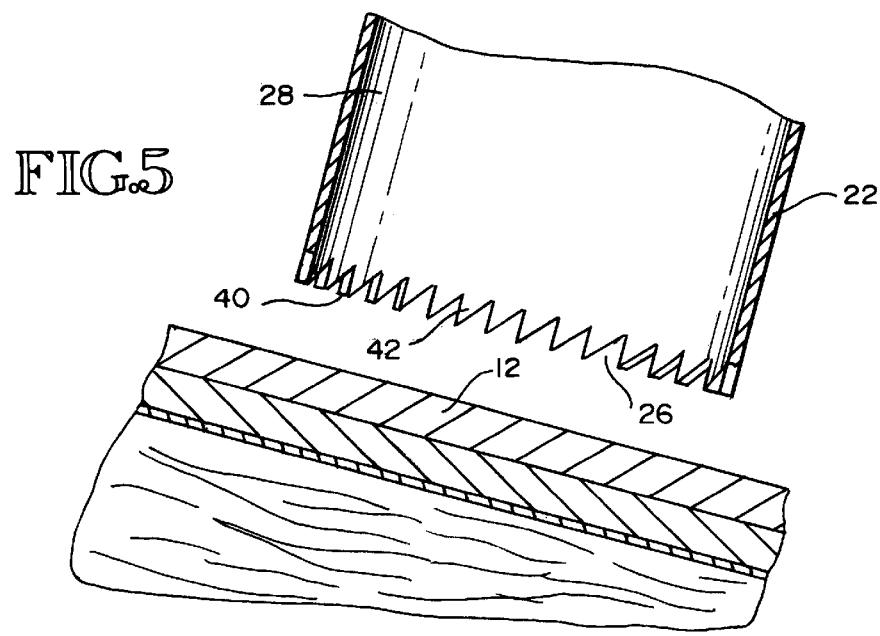

ROOF INSPECTION METHOD

TECHNICAL FIELD

This invention relates to roof care and replacement. More particularly, it relates to a method of inspecting roof covering to determine the thickness of the covering.

BACKGROUND OF THE INVENTION

It is common practice to "re-roof" a house or other building by installing a new roof over the old roof. It is also common practice to do this several times. Eventually, it becomes necessary to remove all of the old roof covering and start over.

There is a need for determining in an easy way the number of layers and the condition of the roof covering without doing much damage to the roof covering in the process. An object of this invention is to provide a method and tool for inspecting a roof to determine the number of existing layers by use of a simple tool that allows the inspection to be made without much damage to the roof covering.

BRIEF SUMMARY OF THE INVENTION

The present invention includes providing a tool that has a tubular body formed by a cylindrical wall having a lower end cutting edge surrounding an inlet leading into a cylindrical inner space inside the body. A handle is provided and is connected to the body. The lower end cutting edge is placed against a roof covering at a location where it is desired to inspect the roof covering. Then, the tool is pushed endwise towards the roof covering while at the same time the handle is turned to rotate the tool and cause the lower end cutting edge to cut a circular kerf in the roof covering. Endwise movement and rotation of the tool are continued until the lower end cutting edge has cut through the roof covering and a disc shaped sample of the roof covering is within the inner space of the tool body. Then, the tool with the roof covering sample inside, is moved out from the roof covering. This leaves an opening in the roof covering. Next, a pusher is used to push the roof covering sample out from the tool. Once accessible, the roof covering sample is inspected to determine the thickness of the roof covering. The sample discloses the number of existing layers of the roof covering.

In preferred form, the lower end cutting edge includes saw teeth constructed and oriented to cut a circular kerf when the tool is rotated.

According to an aspect of the invention, the sample opening is closed or sealed by placing a sealing mastic in the opening.

Another aspect of the invention is to provide the tubular body with diametrically opposed handle openings in the cylindrical wall. A two part handle is used. Each handle part has a main body with a diameter that is larger than the diameter of the openings in the cylindrical wall. One of the handle parts is provided with an axial socket that is in smaller diameter than the openings in the cylindrical wall. The other handle part is provided with an axial extension that is also smaller in diameter than the openings in the cylindrical wall. The inner end of the handle part that includes the socket is positioned against the cylindrical wall with the socket in alignment with the openings in the cylindrical wall. The axial extension on the other handle part is inserted from the other wall openings in the side of the cylindrical wall, first laterally through the tubular body, and then into the axial socket in the first handle part. Once the axial extension has been started in the socket opening, the handle parts are moved together and against the tubular body until the inner end portions of the handle parts are substantially against opposite wall portions of the tubular body.

A further aspect of the invention comprises pulling the two handle parts apart and separating them from the tubular body after the tool and roof covering sample have been removed from the roof covering. Following this separation, the axial extension of the second handle part is inserted into the axial socket of the first handle part. The two handle parts are moved relatively together to move the axial extension into the axial socket and move the inner end portions of the handle parts together. Once the handle parts are united, they may be used as the pusher for pushing the roof covering sample out from the tool.

Other objects, advantages and features of the invention will become apparent from the description of the best mode set forth below, from the drawings, from the claims and from the principles that are embodied in the specific structures that are illustrated and described.

BRIEF DESCRIPTION OF THE SEVERAL VIEWS OF THE DRAWING

Like reference numerals are used to designate like parts throughout the various figures of the drawing, and:

FIG. 3 is a view like FIG. 2, but on a smaller scale, and showing the handle members spaced apart with the tool body between them;

FIG. 4 is a pictorial view of the two handle members secured together apart from the tool body;

FIG. 5 is an enlarged scale view of the lower end cutting portion of the tool body, spaced above a roof covering on a roof;

DETAILED DESCRIPTION OF THE INVENTION

Figure 1:
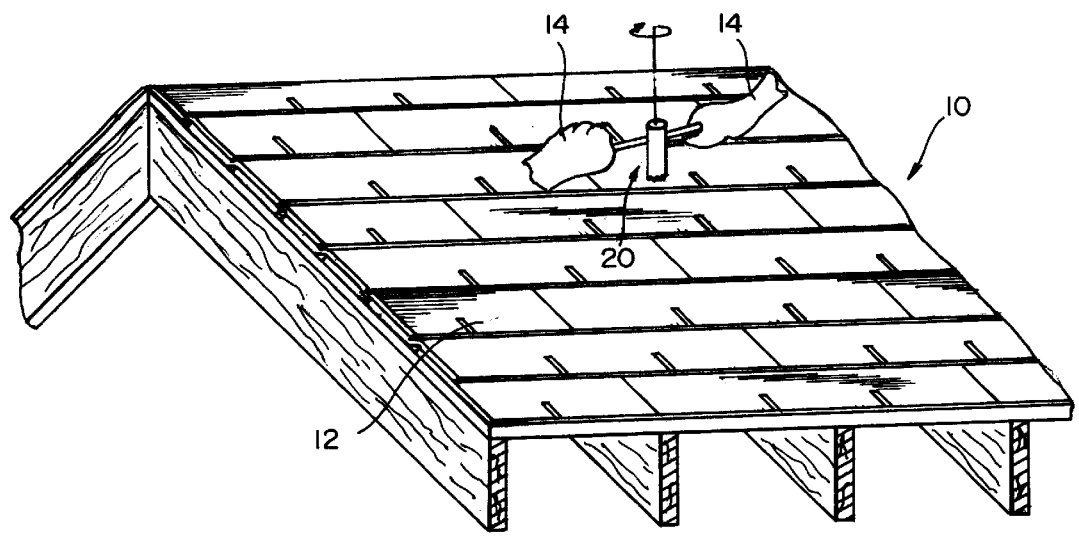
FIG. 1 is a pictorial view of a portion of a roof, such view showing the coring tool of the present invention being held by two hands and in the process of being rotated to cut a core sample from the roof covering.
Figure 2:
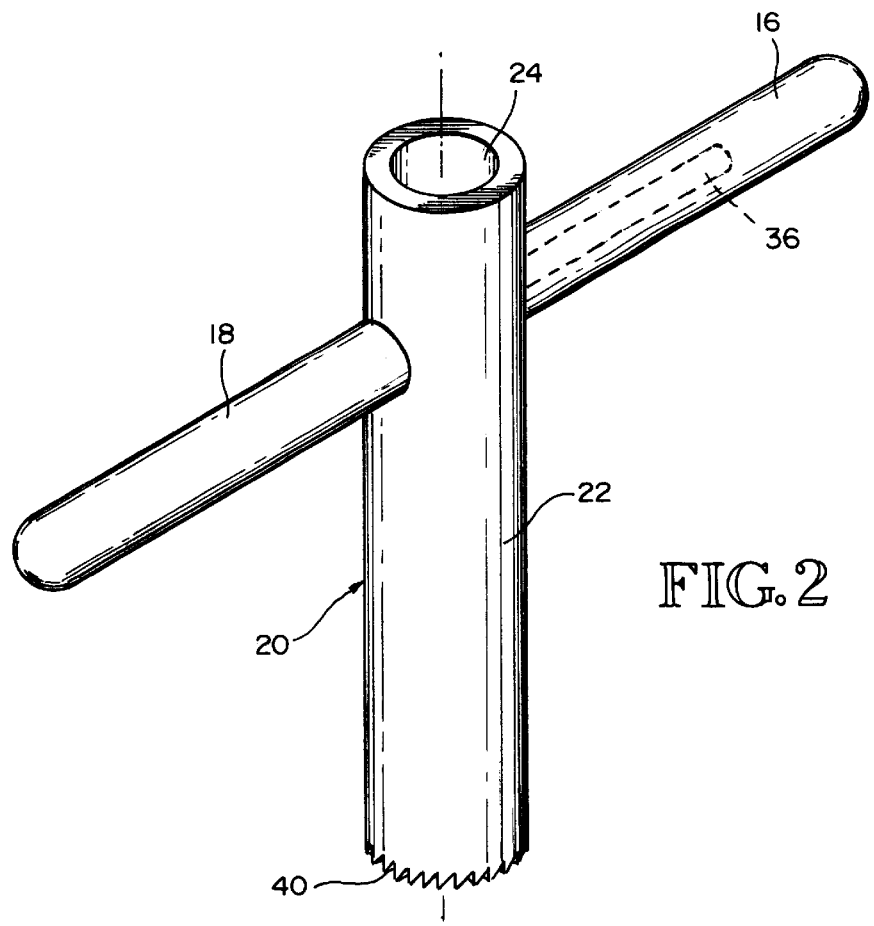
FIG. 2 is a pictorial view of the coring tool, showing the handle members connected to the tool, and the tool ready for use.

FIG. 1 shows, by way of example, the roof inspection process of the present invention being performed on a pitched roof 10 on which the roof covering 12 is made up of asphalt shingles. In FIG. 1, the hands 14 of a user are shown holding handles 16, 18 on a sampling tool 20. Tool 20 comprises a tubular body 22 having open upper and lower ends 24, 26. Tool body 22 has a cylindrical sidewall that defines an inner space 28. Tool body 22 includes a pair of diametrically opposed sidewall openings, one of which is shown in FIG. 3 and is designated 30 in FIG. 3. Handle 16, 18 are separate parts of a handle assembly that is made up of the two parts 16, 18. Thus, handle 16 may be termed a "handle part" and handle 18 may be termed a "handle part." Handle part 16 may have a cylindrical body that is formed to include an axial socket 32. Socket 32 has a socket opening that is at the inner end 34 of the handle part 16. Handle part 18 also has a cylindrical body that is preferably the same size as the handle body of handle part 16. It also has an axial extension 36 that projects endwise from the inner end 38 of the handle body. The two handle bodies are larger in diameter than the sidewall openings 30. Socket 32 and axial extension 36 have diameters that are slightly smaller than the diameter of the openings 30. As shown in FIG. 3, the inner end 34 of handle part 16 is moved towards one of the sidewall openings 30, with the socket 32 aligned with the sidewall opening 30. The handle part 18 is moved towards the opposite sidewall opening 30, with the axial extension 36 in alignment with such sidewall opening 30. The axial extension 36 is inserted into the sidewall opening 30 and the handle part 18 is moved towards the tool body 22. This movement is continued until the axial extension has moved through both sidewall openings 30 and into the socket opening 32 until the inner ends 34, 38 of both handle parts 16, 18 are against the tool body 22 (FIG. 2). At this time, the tool 20 is ready for use.

The tool 20 includes a lower end cutting edge 40. In the preferred embodiment, the cutting edge 40 is shown in the form of saw teeth 42.

Figure 6:
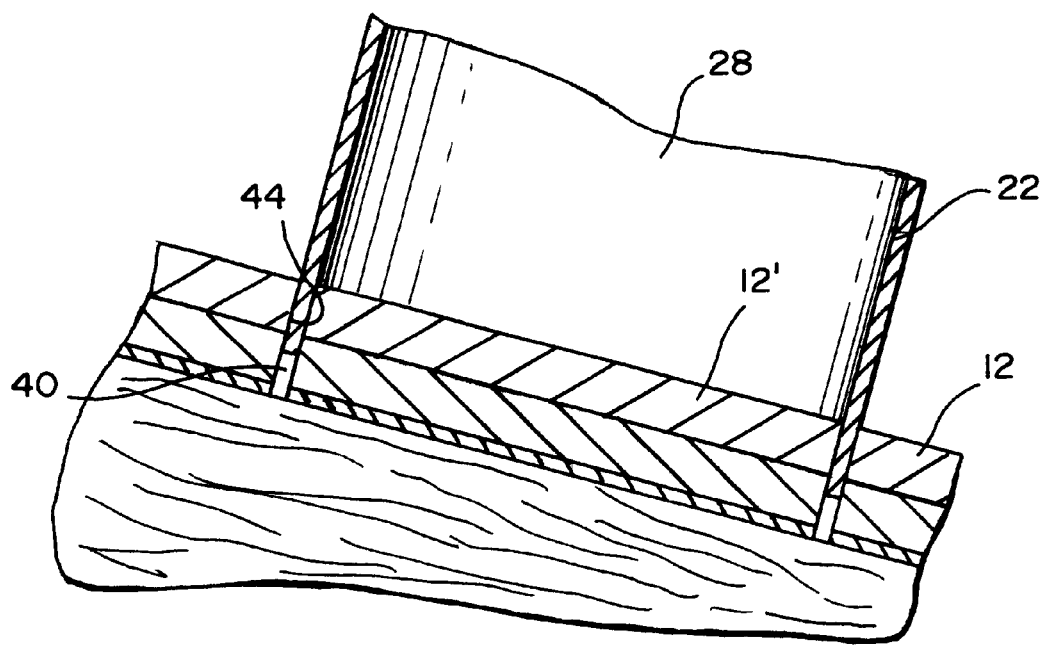
FIG. 6 is a view like FIG. 5, but showing the lower end cutting portion of the cutting tool after it has been rotated to cut its way into the roof covering.
Figure 8:
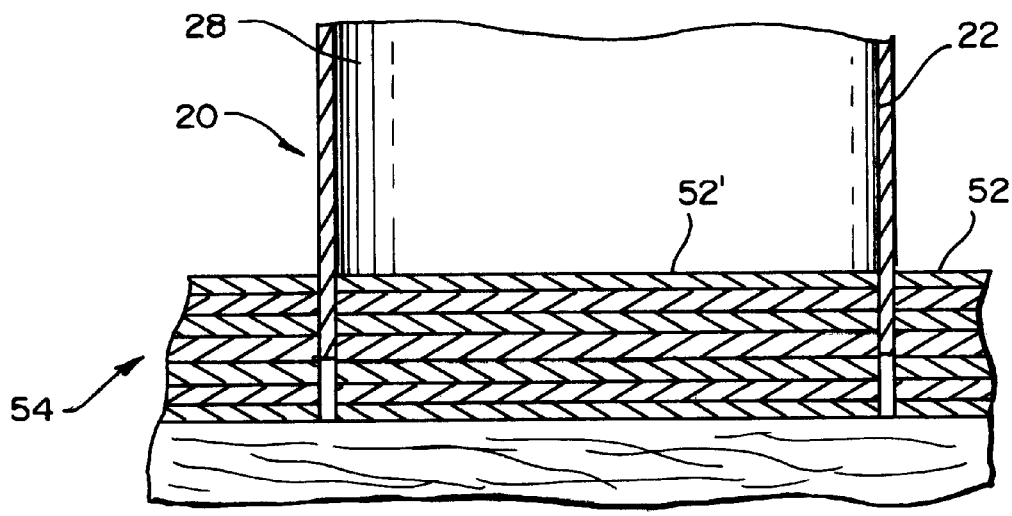
FIG. 8 is a view like FIG. 6, but showing the tool used to cut a sample from the roof covering on a flat roof.

Referring to FIG. 1, the tool 20 is shown set down on the roof covering 12. The tool body 22 is substantially perpendicular to the general plane of the roof covering 12. The user's hands 14 are on the handle bodies of the handle parts 16, 18. The lower end cutting edge 40 is put into contact with the roof covering at the desired location. Then the user both pushes downwardly on the handles 16, 18 and turns them, to cause the tool body 22 to rotate. As tool body 22 rotates, the lower end cutting edge 40 cuts a circular kerf 44 in the roof covering 12. The downward movement and rotation of the tool 20 is continued until the lower end cutting edge 40 has cut its way through the roof covering 12. At that time, a disc shaped sample 12' of the roof covering 12 is within the lower end portion of inner space 20 (FIGS. 6 and 8). Next, the tool 20 is pulled out of the opening 46 that it has cut in the roof covering 12. It carries with it the sample 12'. At this stage, the handles 16, 18 are no longer needed for manipulating the sample tool 20. However, they are needed for another function. They are prepared for this function by separating them from the tool body 22 (FIG. 3). That is, they are pulled apart and separated from the tool body 22. Preferably next, the axial extension 30 is reinserted into the socket 32 and the handle part 16, 18 are again moved towards each other. Movement is continued until the movement stops. (FIG. 4). Now, the united handle parts 16, 18 become a pusher. This pusher 16, 18 is inserted into the upper end opening 24 in the tool body 22. It is moved axially until it contacts the sample 12' at the lower end of the tool body 22. It is then moved a further amount for the purpose of pushing the sample 12' out from the tool body 22.

Figure 7:
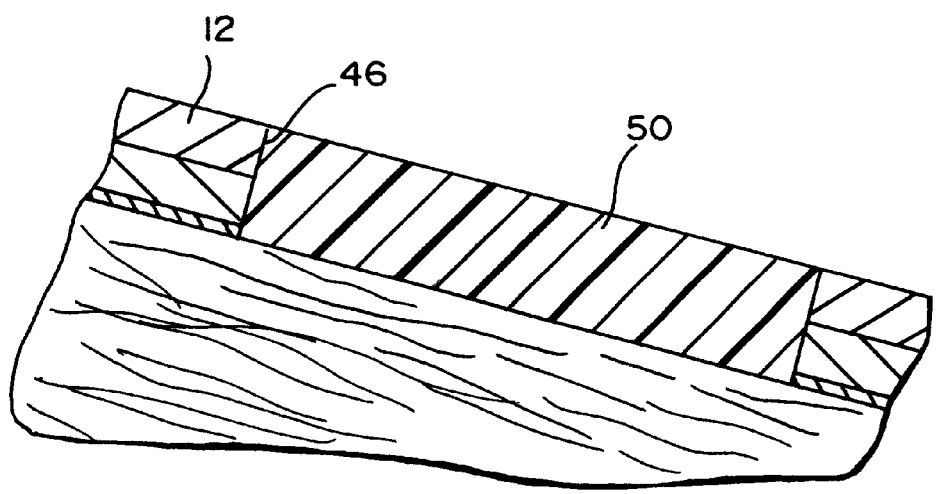
FIG. 7 is a view like FIGS. 5 and 6, but showing a plug of material within the opening that was formed in the roof covering by the coring tool.

Once the sample 12' is accessible, it is closely examined to determine the thickness of the roof covering 12. It is also possible to look into the opening 46 to inspect the condition of the roof covering 12 at the boundaries of the opening 46. Then can be easily done by inserting a suitable roofing mastic into the opening 46 to create a plug 50 that closes the opening and seals between itself and the cut edge boundary of the opening 46. This is shown in FIG. 7.

Figure 9:
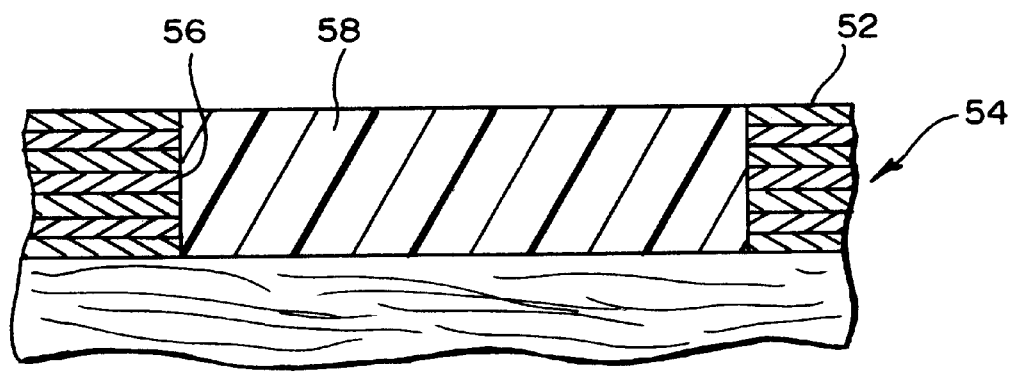
FIG. 9 is a view like FIG. 7, but showing a closure plug in the sample opening in the roof covering on a flat roof.

FIG. 8 shows the tool 20 being used to cut a sample 52' from a roof covering 52 on a flat roof 54. The procedure is the same as described above in connection with FIGS. 5–7. The main difference is that the different type of roof covering requires a different evaluation of the roof covering. Then, a suitable mastic is introduced into the sample opening 56 to form a closure and sealing plug 58 (FIG. 9).

Experienced roofers will know what to look for when inspecting the sample that has been removed from the roof covering and/or the edges of the sample opening. This is true regardless of the type of roof covering that is being inspected.

The illustrated embodiments are only examples of the present invention and, therefore, are non-limitive. It is to be understood that many changes in the particular structure, materials and features of the invention may be made without departing from the spirit and scope of the invention. Therefore, it is my intention that my patent rights not be limited by the particular embodiments illustrated and described herein, but rather determined by the following claims, interpreted according to accepted doctrines of claim interpretation, including use of the doctrine of equivalents and reversal of parts.

What is claimed is:

1. A roof inspection and repair method, comprising:

providing a tool that has a tubular body formed by a cylindrical wall having a lower end cutting edge surrounding an inlet leading into a cylindrical inner space inside the body;

providing the tubular body with diametrically opposite openings in the cylindrical wall where it is desired to provide a handle, providing a two part handle, with each handle part having a body with a diameter larger than the diameter of the openings in the cylindrical wall;

providing an axial socket in the body of a first of the handle parts that is of a diameter smaller than the openings in the cylindrical wall;

providing the body of the other, second handle part with an axial extension that is smaller in diameter than the openings in the cylindrical wall;

moving the first handle part towards the cylindrical wall, with its socket opening in alignment with one of the openings in the cylindrical wall;

inserting the axial extension on the other handle part through the other opening in the cylindrical wall, and moving it first laterally through the cylindrical wall and then into the axial socket in the first handle part;

continue movement of the second handle parts until inner end portions of the handle part are substantially against opposite wall portions of the tubular body;

placing the lower end cutting edge on a roof covering at a location where it is desired to inspect the roof covering;

pushing the tool endwise towards the roof covering while at the same time using the handle to rotate the tool and cause the lower end cutting edge to cut a circular kerf in the roof covering;

continuing endwise movement and rotation of the tool until the lower end cutting edge has cut through the roof covering and a disc shaped sample of the roof covering is within the inner space of the body;

removing the tool and roof covering sample out from the roof covering, leaving an opening in the roof covering;

pulling the two handle parts apart and separating them from the tubular tool body after removing the tool and roof covering sample out from the roof covering;

inserting the axial extension of the second handle part into the axial socket of the first handle part;

moving the two handle parts relatively together to move the axial extension into the axial socket and moving inner end portions of the handle parts together to form a pusher;

inserting the pusher into an end opening in the tool and moving it through the tool and against the roof covering sample that is inside the tool;

using the pusher to push the roof covering sample out from the tool; and inspecting the sample of roof covering material to determine a condition of the roof covering material.

2. The method of claim 1, further comprising, inserting a plug of material into the opening in the roof covering that was formed by the tool.

3. The method of claim 2, comprising placing a sealing mastic in the opening to form the plug.

* * * * *